United States Patent
Wang et al.

(10) Patent No.: US 9,326,508 B2
(45) Date of Patent: May 3, 2016

(54) (S)-3'-METHYL-ABSCISIC ACID AND ESTERS THEREOF

(71) Applicant: Valent BioSciences Corporation, Libertyville, IL (US)

(72) Inventors: Gary Wang, Libertyville, IL (US); Daniel F. Heiman, Libertyville, IL (US); Gregory D. Venburg, Deerfield, IL (US)

(73) Assignee: Valent BioSciences Corporation, Libertyville, IL (US)

(*) Notice: Subject to any disclaimer, the term of this patent is extended or adjusted under 35 U.S.C. 154(b) by 0 days.

(21) Appl. No.: 14/593,597

(22) Filed: Jan. 9, 2015

(65) Prior Publication Data
US 2015/0197479 A1 Jul. 16, 2015

Related U.S. Application Data

(60) Provisional application No. 61/925,764, filed on Jan. 10, 2014.

(51) Int. Cl.
| | |
|---|---|
| *A01N 37/06* | (2006.01) |
| *C07C 59/90* | (2006.01) |
| *C07C 51/347* | (2006.01) |
| *C07C 69/738* | (2006.01) |
| *C07C 67/30* | (2006.01) |
| *C07C 403/20* | (2006.01) |
| *A01N 37/42* | (2006.01) |

(52) U.S. Cl.
CPC ............... *A01N 37/06* (2013.01); *A01N 37/42* (2013.01); *C07C 403/20* (2013.01); *C07C 2101/16* (2013.01)

(58) Field of Classification Search
None
See application file for complete search history.

(56) References Cited

U.S. PATENT DOCUMENTS

| | | | |
|---|---|---|---|
| 5,518,995 | A | 5/1996 | Abrams et al. |
| 6,004,905 | A | 12/1999 | Abrams et al. |
| 8,536,224 | B2 | 9/2013 | Herrero et al. |
| 2008/0200339 | A1 | 8/2008 | Abrams et al. |
| 2010/0152046 | A1 | 6/2010 | Belkind et al. |
| 2013/0158098 | A1 | 6/2013 | Liang et al. |
| 2013/0291227 | A1 | 10/2013 | Buysse et al. |

FOREIGN PATENT DOCUMENTS

| | | |
|---|---|---|
| WO | WO 2005/108345 | 11/2005 |
| WO | WO 2013/123164 | 8/2013 |

OTHER PUBLICATIONS

ISR and Written Opinion in corresponding Application No. PCT/US2015/010726 issued Apr. 6, 2015.
Todoroki et al., "8'8'-Difluoro- and 8',8',-Trifluoroabscisic Acids as Highly Potent, Long-Lasting Analogues of Abscisic Acid" Phytochemistry, 1995, vol. 38, No. 3, pp. 561-568.
Todoroki et al., "Synthesis and biological activity of 1'-deoxy-1'-fluoro-and 8'-fluoroabscisic acids", Phytochemistry, 1995, vol. 40, No. 3, pp. 633-641.

(Continued)

*Primary Examiner* — Mina Haghighatian
*Assistant Examiner* — Erin Hirt
(74) *Attorney, Agent, or Firm* — Wood, Phillips, Katz, Clark & Mortimer

(57) ABSTRACT

The invention relates to (S)-3'-methyl-abscisic acid, and esters thereof, and methods of using and making these compounds.

9 Claims, 1 Drawing Sheet

*Arabidopsis* seed germination in the presence of 0.3 ppm (*S*)-ABA and analogs

(56) References Cited

OTHER PUBLICATIONS

Nakano et al., "Synthesis and biological activity of 7'-, 8'-, and 9'-alkyl analogues of abscisic acid", Biosci. Biotech. Biochem, 1995, 59(9), pp. 1699-1706.

Todoroki et al., "8'- and 9'-Methoxyabscsic acids as antimetabolic analogs of abscisic acid", Biosci. Biotech. Biochem., 1994, 59(4), pp. 707-715.

Todoroki et al., "Synthesis and biological activities of 8'-methylene- and 8'-methylidyneabscisic acids", Biosci. Biotech. Biochem., 1997, 61(12), pp. 2043-2045.

Todoroki et al., "Ring conformational requirement for biological activity of abscisic acid probed by the cyclopropane analogues", Tetrahedron, 1996, vol. 52, No. 24, pp. 8081-8098.

Todoroki et al., "Synthesis, biological activity and metabolism of (S)-(+)-3'-Fluoroabscsic acid", Tetrahedron 1995, vol. 51, No. 25, pp. 6911-6926.

Arai et al., "Synthesis and biological activity of 3'-chloro, -bromo, and -iodoabscisic acids, and biological activity of 3'-fluoro-8'hydroxyabscsic acid" Phytochemistry 1999, 52, pp. 1185-1193.

Balsevich et al., "Activity and utility of abscisic acid having a 3' thioether lonker arm*", Phytochemistry 1997, vol. 44, No. 2, pp. 215-220.

Todoroki et al., "Synthesis of isomerization process of 8'-hydroxyabscisic acid and its 3'-fluorinated analog in aqueous solutions", Tetrahedron 2000, 56, pp. 1649-1653.

Todoroki et al., "3'-Azidoabscisic acid as a photoaffinity reagent for abscisic acid binding proteins", Bioorganic & Medicinal Chemistry Letters 2001, 11, pp. 2381-2384.

Priest et al., "The use of abscisic acid analogues to analyse the substrate selectivity of UGT71B6, a UDP-glycosyltransferase of Arabidopsis thaliana", FEBS Letters 2005, 579, pp. 4454-4458.

Nyangulu et al., "Synthesis and biological activity of tetralone abscisic acid analogues", Org. Biomol. Chem., 2006, 4, pp. 1400-1412.

Nyangulu et al., "An affinity probe for isolation of abscisic acid-binding proteins", J. Am. Chem. Soc. 2005, 127, pp. 1662-1664.

Ueno et al., "Differences between the structural requirements for ABA 8'-hydroxylase inhibition and for ABA activity", Bioorganic & Medicinal Chemistry 2005, 13, pp. 3359-3370.

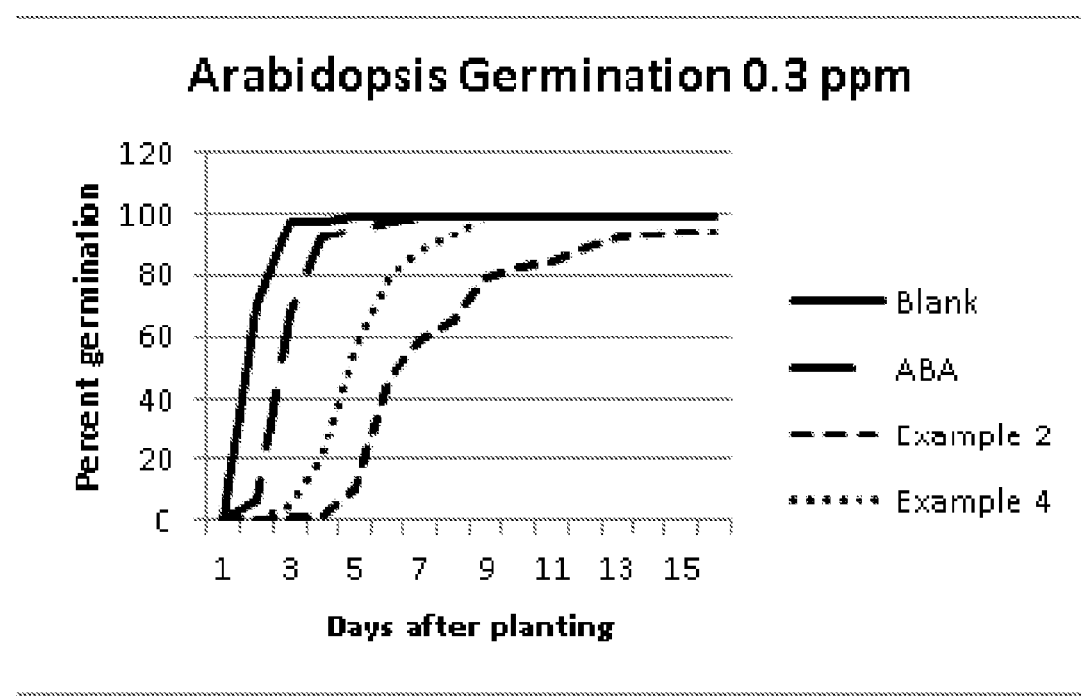
*Arabidopsis* seed germination in the presence of 0.3 ppm (*S*)-ABA and analogs

(S)-3'-METHYL-ABSCISIC ACID AND ESTERS THEREOF

CROSS-REFERENCE TO RELATED APPLICATION

This application claims priority of U.S. Provisional Application 61/925,764 filed Jan. 10, 2014, the disclosure of which is incorporated herein by reference.

FIELD OF THE INVENTION

The present invention is directed to (S)-3'-methyl-abscisic acid ("(S)-3'-methyl-ABA") and esters thereof, and methods for using and synthesizing these compounds.

BACKGROUND OF THE INVENTION

Abscisic acid ("ABA") is a naturally occurring plant growth regulator that regulates a wide range of plant physiological processes such as seed germination, seedling elongation, abiotic stress response, flowering, and fruit development. The naturally occurring and biologically active form of ABA is the S enantiomer, (S)-abscisic acid ("(S)-ABA"). Consequently, a variety of commercial utilities have been identified for (S)-ABA in horticulture and agronomy. (S)-ABA exerts its biological activities by binding to (S)-ABA receptors and activating cellular signal transduction cascades. In addition, (S)-ABA has been demonstrated to have pharmaceutical and nutraceutical utilities (see U.S. Pat. No. 8,536,224).

Synthetic analogs of ABA may exhibit biological activities either similar to (S)-ABA but with altered (enhanced) potency (ABA agonists) or with a differing spectrum of affinity for the multiple ABA receptors than (S)-ABA itself has. The synthetic analogs may also possess improved uptake by plant tissues as well as enhanced metabolic stability. Additionally, synthetic analogs may have better chemical and environmental stability than (S)-ABA. Thus, synthetic ABA analogs may possess unique biological activities and have been pursued as an approach to identify novel plant growth regulators.

A variety of synthetic analogs of ABA have been revealed in the public domain. Several Japanese research groups have synthesized ABA analogs with modifications of the side chain and/or with cyclohexenone ring substituents through de novo synthesis (Y. Todoroki, et al. *Phytochem.* 1995, 38, 561-568; Y. Todoroki, et al. *Phytochem.* 1995, 40, 633-641; S, Nakano, et al. *Biosci. Biotech. Biochem.* 1995, 59, 1699-176; Y. Todoroki, et al. *Biosci. Biotech. Biochem.* 1994, 58, 707-715; Y. Todoroki, et al. *Biosci. Biotech. Biochem.* 1997, 61, 2043-2045; Y. Todoroki, et al. *Tetrahedron,* 1996, 52, 8081-8098). Synthesis of (S)-3'-halogen-ABA, (S)-3'-azido-ABA and (S)-3'-alkylthio-ABA from (S)-ABA have also been reported (Y. Todoroki, et al. *Tetrahedron,* 1995, 51, 6911-6926; S. Arai, et al. *Phytochem.* 1999, 52, 1185-1193; J. J. Balsevich, et al. *Phytochem.* 1977, 44, 215-220; Y. Todoroki, et al. *Tetrahedron,* 2000, 56, 1649-1653; Y. Todoroki, et al. *Bioorg. Med. Chem. Lett.* 2001, 11, 2381-2384). The work done by S. R. Abrams and coworkers at the Plant Biotechnology Institute at National Research Council of Canada is also noteworthy. Using de novo synthesis approaches, ABA analogs with modified side-chains or $C_6'$-substitution have been prepared either as racemic mixtures or, in some cases, as pure stereoisomers (see U.S. Pat. No. 5,518,995; D. M. Priest, et al. *FEBS Letters,* 2005, 579, 4454-4458). A tetralone series of analogs in which the cyclohexenone ring of (S)-ABA is replaced with a bicyclic tetralone ring have also been described (J. M. Nyangulu, et al. *Org. Biomol. Chem.* 2006, 4, 1400-1412; J. M. Nyangulu, et al. *J. Am. Chem. Soc.* 2005, 127, 1662-1664; WO2005/108345).

The synthetic ABA analogs reported in the literature are limited in scope and are often prepared via multi-step de novo synthesis. The syntheses generally suffer from low overall yields, particularly when the optically pure single enantiomers are desired. Thus, these compounds are generally expensive to synthesize in large amounts or to manufacture on a commercial scale, limiting their commercial application. The (S)-ABA analogs of the present invention possess the aforementioned biological activities and, more importantly, can be prepared efficiently from (S)-ABA, which until recently was not available in large quantities.

The biological activity of racemic (±)-3'-methyl-ABA has been briefly described in a publication (K. Ueno, et al. *Bioorg. Med. Chem.* 2005, 13, 3359-3370), but the synthesis of this compound has not been reported. According to Ueno, et al., (±)-3'-methyl-ABA showed equal activity to (S)-ABA in a rice seedling elongation assay and weaker activity than (S)-ABA in an (S)-ABA 8'-hydroxylase inhibition assay. In addition, a structure that could be interpreted as representing (S)-3'-methyl-ABA was printed in a paper (Y. Todoroki, et al. *Bioorg. Med. Chem. Lett,* 2001, 11, 2381-2384), but neither the synthesis nor any biological data for that compound has been described in the public domain. Thus, there is no prior art in the public domain that enables the synthesis of (S)-3'-methyl-ABA and esters thereof or teaches the biological activities of (S)-3'-methyl-ABA and its esters. Most importantly, it was not obvious to those of skill in the art at the time of the invention, based on all available information in the public domain (vide supra), that (S)-3'-methyl-ABA would offer any advantage over (S)-ABA or (±)-3'-methyl-ABA.

Accordingly, there is a need for entantiomerically pure (S)-3'-methyl-ABA analogs which may be agonists of (S)-ABA and have improved biological activity. There is also a need for methods to prepare (S)-3'-methyl-ABA and esters thereof.

BRIEF DESCRIPTION OF THE DRAWINGS

FIG. 1. *Arabidopsis* seed germination in the presence of 0.3 ppm (S)-ABA and analogs, is a graph produced from the data from the Seed Germination Assay described in Example 5 below.

SUMMARY OF THE INVENTION

Applicants have discovered enantiomerically pure (S)-3'-methyl-abscisic acid and esters thereof and a method for synthesizing these compounds.

In one aspect, the present invention is directed to the compound of Formula I:

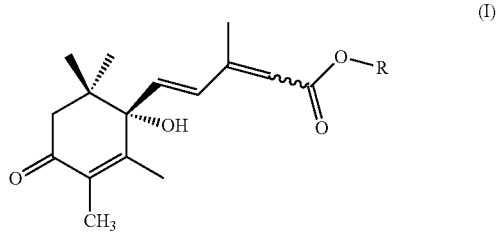

wherein R is hydrogen, substituted or unsubstituted alkyl, cycloalkyl, heterocycloalkyl, alkenylalkyl, alkynylalkyl, alkenyl, cycloalkenyl, heterocycloalkenyl, alkynyl, aryl, heteroaryl, arylalkyl, or heteroarylalkyl;
and salts thereof.

In another aspect, the invention is directed to method for regulating plant growth comprising applying an effective amount of any compound of the present invention to a plant in need of growth regulation.

In a further aspect, the invention is directed toward an efficient method for preparing the compound of the present invention by chemical synthesis.

DETAILED DESCRIPTION OF THE INVENTION

The compounds of the present invention are (S)-ABA analogs that are enantiomerically pure and relatively easy to synthesize. The synthesis scheme of the present invention also provides good yield.

In one embodiment, the invention is directed to compound of Formula I:

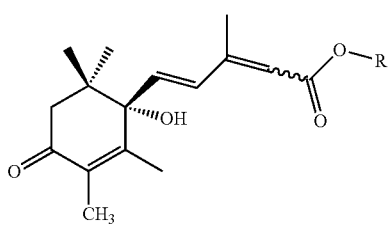

(I)

wherein R is hydrogen, substituted or unsubstituted alkyl, cycloalkyl, heterocycloalkyl, alkenylalkyl, alkynylalkyl, alkenyl, cycloalkenyl, heterocycloalkenyl, alkynyl, aryl, heteroaryl, arylalkyl, or heteroarylalkyl;
and salts thereof.

In a preferred embodiment, R is hydrogen.

In another preferred embodiment, R is alkyl. In a more preferred embodiment, R is lower alkyl.

As used herein, a substituted compound is one in which one or more hydrogen atoms of a core structure have been replaced with a functional group such as an alkyl, hydroxyl, or halogen. An example of a substituted benzene is toluene ($C_6H_5$—$CH_3$).

As used herein, alkyl refers to a straight or branched chain alkane radical (i.e. a group missing one of the hydrogen atoms required for a stable structure), (—$C_nH_{2n+1}$). Examples of alkyls include methyl, ethyl, propyl, iso-propyl, butyl, sec-butyl, pentyl, hexyl, heptyl, octyl, nonyl, decyl, undecyl, and dodecyl. A "lower alkyl" refers to an alkyl containing 1 to 6 carbons. Cycloalkyl refers to an alicyclic hydrocarbon. Examples of cycloalkyls include cyclopropyl, cyclobutyl, cyclopentyl, cyclohexyl, cycloheptyl. As used herein, heterocycloalkyl refers to a cyclic alkyl with an element other than carbon in the ring. Preferred alkyls are lower alkyls.

As used herein, alkenyl refers to aliphatic hydrocarbon radicals derived from alkenes by removing a vinyl proton, preferably having from 2 to 40 carbon atoms, more preferably 2 to 20 carbon atoms and even more preferably 2 to 6 carbon atoms. As used herein, cycloalkenyl refers to an alicyclic alkenyl. Heterocycloalkenyl refers to a cyclic alkenyl with an element other than carbon in the ring. Representative alkenyl groups include vinyl (—CH=$CH_2$) and Z- or E-1-buten-1-yl (—CH=$CHCH_2CH_3$).

The term alkynyl used herein refers to a monoradical derived from an alkyne by removing one of the alkynylic proton, preferably having from 2 to 40 carbon atoms, more preferably 2 to 20 carbon atoms and even more preferably 2 to 6 carbon atoms. Preferred alkynyl groups include ethynyl (—C≡CH), 1-propyn-1-yl (—C≡$CCH_3$) and the like.

The term alkenylalkyl used herein refers to an alkyl group comprising at least one carbon-carbon double bond at a position remote from the point of attachment. An example of an alkenylalkyl group is 2-propen-1-yl (—$CH_2$CH=$CH_2$, a.k.a. allyl).

The term alkynylalkyl used herein refers to an alkyl group comprising at least one carbon-carbon triple bond at a position remote from the point of attachment. An example of alkynylalkyl is 2-propyn-1-yl (—$CH_2$C≡CH, a.k.a. propargyl).

The term aryl used herein refers to an substituted or unsubstituted aromatic carbocyclic group of from 6 to 20 carbon atoms having a single ring (for example, phenyl) or multiple condensed (fused) rings, wherein at least one ring is aromatic (for example, naphthyl, dihydrophenanthrenyl, fluorenyl, or anthryl). Preferred aryls include phenyl, naphthyl and the like.

As used herein, heteroaryl refers to an aromatic cyclic group with an element other than carbon in a 5- or 6-membered ring or in at least one of several condensed 5- or 6-membered rings. Representative heteroaryl groups include pyridyl, oxazolyl, and thiazolyl.

As used herein, cyano refers to a radical with the formula —C≡N.

The term halogen as used herein refers to fluorine, chlorine, bromine and iodine. Embodiments of the present invention may also include di or trihalogens.

As used herein "salts" refers to those salts which retain the biological effectiveness and properties of the parent compounds and which are not biologically or otherwise harmful at the dosage administered. Salts of the compounds of the present inventions may be prepared from inorganic or organic acids or bases.

In another embodiment, the invention is directed to the compound of Formula I:

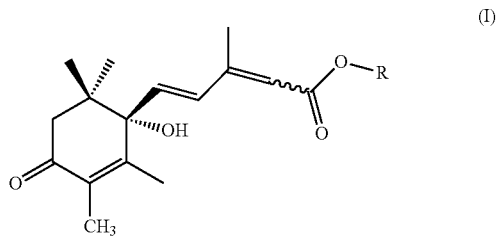

(I)

wherein R is independently substituted with at least one of —OH, —$NH_2$, —SH, halogen, —CN, —$NR^1R^2$, —$OR^1$, —$SR^1$, —S(O)$R^1$, —$SO_2R^1$, —C(O)$R^1$, —C(O)$NR^1R^2$, —NHC(O)$R^1$, —$NHSO_2R^1$, —NHC(O)$OR^3$, —$SO_2NR^1R^2$, or —NHC(O)$NR^1R^2$ wherein $R^1$ and $R^2$ are each independently hydrogen or lower alkyl and $R^3$ is lower alkyl.

In a further embodiment, the salt of the present invention comprises an inorganic cation including, but not limited to, alkali or alkaline earth metal cations, such as $Na^+$, $K^+$, $Li^+$, $Mg^{2+}$, $Ca^{2+}$, or an organic cation such as a protonated amine ($^+NHR^4R^5R^6$), wherein $R^4$, $R^5$, and $R^6$ are each independently hydrogen, lower alkyl, aralkyl or a quaternary ammonium ion)($^+NR^7R^8R^9R^{10}$ wherein $R^7$, $R^8$, $R^9$, and $R^{10}$ are each independently aralkyl or lower alkyl.

In yet another embodiment, the salt of the present invention comprises inorganic anion selected from the group consisting of chloride ($Cl^-$), bromide ($Br^-$), iodide ($I^-$), sulfate ($SO_4^{2-}$), and bisulfate ($HSO_4$—), and the like, or an organic anion selected from the group consisting of formate ($HCO_2^-$), acetate ($CH_3CO_2^-$), tartrate ($^-CO_2CH(OH)CH(OH)CO_2^-$), methanesulfonate ($CH_3SO_3^-$) and tolylsulfonate ($CH_3C_6H_4SO_3^-$), and wherein R must contain a basic nitrogen atom.

In yet another embodiment, the invention is directed to methods for regulating plant growth comprising applying an effective amount of the compounds of the present invention to a plant or a plant part in need of growth regulation.

In another embodiment, the invention is directed to processes for making the compounds of the present invention which includes reacting (S)-ABA with an alkylating agent to form an ester (Step a); treating the (S)-ABA ester resulting from Step a with a base and a methylating agent in a solvent (Step b); and optionally hydrolyzing the compounds resulting from Step b using an ester hydrolysis procedure. Any ester hydrolysis procedure known by those of skill in the art can be used. These procedures include using LiOH, NaOH, or KOH in aqueous methanol, enzymatic hydrolysis with hydrolases in water optionally combined with miscible organic solvent. This synthesis is illustrated in Scheme I below.

Scheme I:

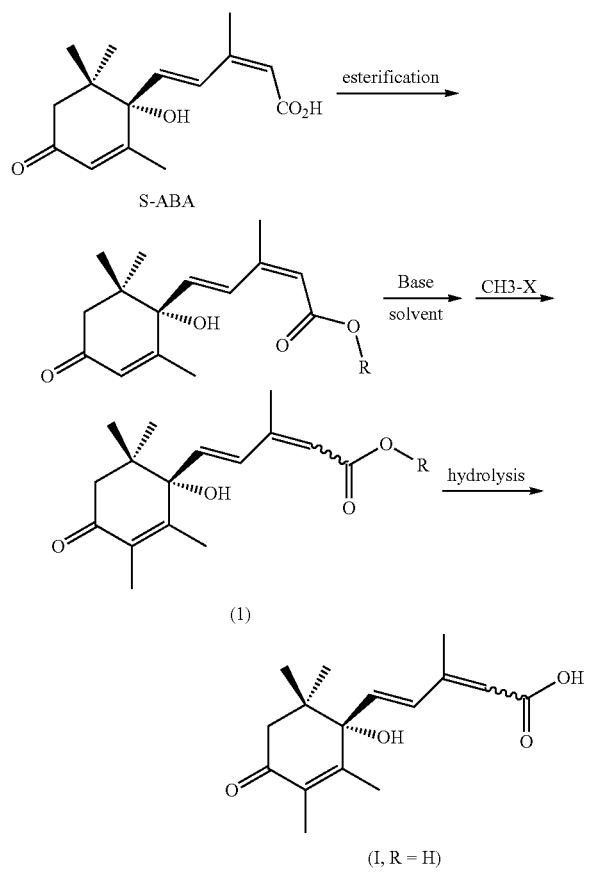

The compounds of the present invention have a wide range of commercial utilities, including fruit (e.g. grapes) coloration, thinning, bud breaking, seed treatment, and crop stress management. Additionally, these compounds may have utility in the nutraceutical and pharmaceutical areas.

The disclosed embodiments are simply exemplary embodiments of the inventive concepts disclosed herein and should not be considered as limiting, unless the claims expressly state otherwise.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a", "an" and "the" are intended to include the plural as well as the singular, unless the context clearly indicates otherwise.

The following examples are intended to illustrate the present invention and to teach one of ordinary skill in the art how to use the formulations of the invention. They are not intended to be limiting in any way.

EXAMPLES

Example 1a

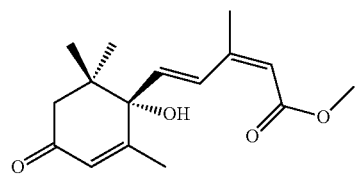

(2Z,4E)-methyl 5-((S)-1-hydroxy-2,6,6-trimethyl-4-oxocyclohex-2-en-1-yl)-3-methylpenta-2,4-dienoate A solution of (S)-ABA (53 g, 0.2 mole) in acetonitrile (800 ml) was cooled with an ice bath. Cesium carbonate (98 g, 0.3 mole) was added. The mixture was stirred for ten minutes, than methyl iodide (24.8 ml, 56.5 g, 0.4 mole) was added. After stirring at ambient temperature overnight, the mixture was concentrated to ~300 ml and water (500 ml) was added. The resulting mixture was extracted with ethyl acetate (3×200 ml). The resulting organic solution was washed twice with saturated aqueous sodium sulfite solution, dried (anhydrous $MgSO_4$) and filtered. Evaporation of the filtrate gave the title compound as an off-white solid (56 g). $^1$HNMR ($CDCl_3$): δ7.90 (d, 1H), 6.15 (d, 1H), 5.95 (s, 1H), 5.76 (s, 1H), 3.71 (s, 3H), 2.48 (d, 1H), 2.29 (d, 1H), 2.01 (s, 3H), 1.93 (s, 3H), 1.11 (s, 3H), 1.02 (s, 3H).

Example 1

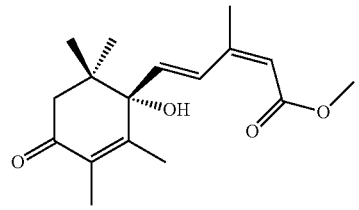

(2Z,4E)-methyl 5-((S)-1-hydroxy-2,3,6,6-tetramethyl-4-oxocyclohex-2-en-1-yl)-3-methylpenta-2,4-dienoate A solution of Example 1a (27.8 g, 0.1 mole) in anhydrous tetrahydrofuran (THF, 600 ml) was cooled to 0° C. with an ice bath under an atmosphere of nitrogen. Lithium hexamethyl disilazane (1.0 M solution in THF, 150 ml) was added dropwise via a syringe over about 30 minutes. The resulting solution was stirred at 0° C. for 30 minutes and the ice bath was removed. A solution of methyl iodide (8.09 ml, 18.4 g, 0.13 mole) in anhydrous THF (20 ml) was added via a syringe over 20 minutes. The resulting solution was stirred at ambient temperature overnight. The reaction was quenched with saturated aqueous ammonium chloride solution (200 ml) and water (200 ml) and extracted with ethyl acetate (3×150 ml). The combined organic solution was dried (MgSO$_4$), filtered and concentrated. The residue was purified on a silica gel column eluted with ethyl acetate and hexane. The title compound was obtained as a white solid (17.1 g). $^1$HNMR (CDCl$_3$): δ7.84 (d, 1H), 6.16 (d, 1H), 5.75 (s, 1H), 3.70 (s, 3H), 2.44 (d, 1H), 2.34 (d, 1H), 2.00 (s, 3H), 1.88 (s, 3H), 1.83 (s, 3H), 1.07 (s, 3H), 1.00 (s, 3H). MS (ESI—): m/e=291.

Example 2

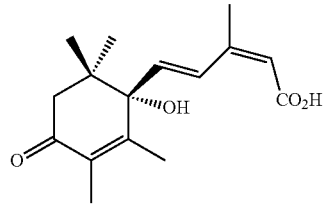

(2Z,4E)-((S)-1-hydroxy-2,3,6,6-tetramethyl-4-oxo-cyclohex-2-en-1-yl)-3-methylpenta-2,4-dienoic acid (3'-methyl-(S)-abscisic acid)

To a solution of Example 1 (17.1 g, 58.5 mmole) in methanol (270 ml) and water (30 ml) was added lithium hydroxide mono-hydrate (9.81 g, 234 mmole). The mixture was stirred at room temperature for 48 hours, than evaporated to removed most of methanol. Water (200 ml) was added. The resulting mixture was cooled with an ice bath and acidified with 6N aqueous HCl to pH 2-3, resulting in a white precipitation. The mixture was extracted with ethyl acetate (3×150 ml). The combined organic solution was dried (MgSO$_4$), filtered and evaporated to give the title compound as a white solid (16.4 g). Alternatively, the white precipitate can be directly harvested from the acidified aqueous solution by filtration, washed with small amount of water, and dried under vacuum to give the title compound. $^1$HNMR (CDCl$_3$): δ7.89 (d, 1H), 6.17 (d, 1H), 5.76 (s, 1H), 2.47 (d, 1H), 2.34 (d, 1H), 2.15 (s, 1H), 2.10 (s, 3H), 1.87 (s, 3H), 1.83 (s, 3H), 1.07 (s, 3H), 1.01 (s, 3H). MS (ESI—): m/e=277. 2D-NMR experiments (COSY, NOESY, HSQC, HMBC) established that the methylation occurred at the 3'-position. Chiral HPLC analysis on a Pirkle Covalent (R,R)-Whelk-01 column indicates that this material is >99% (S)-isomer. The (R)-isomer is below the detection limit of a UV-detector set at 262 nm.

Example 3a

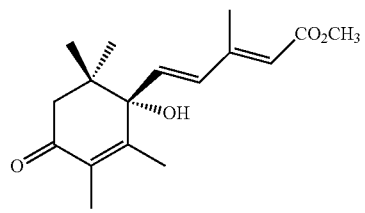

(2E,4E)-methyl 5-((S)-1-hydroxy-2,3,6,6-tetramethyl-4-oxocyclohex-2-en-1-yl)-3-methylpenta-2,4-dienoate This compound was isolated as a by-product during the preparation of Example 1.

Example 3

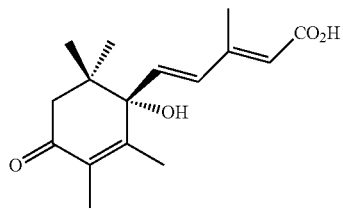

(2E,4E)-((S)-1-hydroxy-2,3,6,6-tetramethyl-4-oxo-cyclohex-2-en-1-yl)-3-methylpenta-2,4-dienoic acid The title compound was prepared according to the procedure of Example 2, substituting Example 3a for Example 1. $^1$HNMR (CDCl$_3$): δ6.43 (d, 1H), 6.17 (d, 1H), 5.87 (s, 1H), 2.46 (d, 1H), 2.35 (d, 1H), 2.29 (s, 3H), 2.11 (s, 1H), 1.85 (s, 3H), 1.82 (s, 3H), 1.06 (s, 3H), 100 (s, 3H). MS (ESI—): m/e=277. 2D-NMR experiments (COSY, NOESY, HSQC, HMBC) established that the alkylation occurred at the 3'-position.

Example 4

(±)-3'-methyl ABA for Comparison

Example 4a

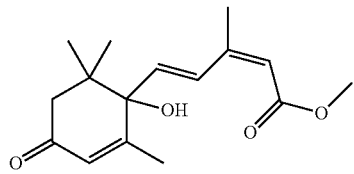 [SMILES: COC(=O)/C=C(C)\C=C\C1(O)C(C)=CC(=O)CC1(C)C]

(±)-(2Z,4E)-methyl 5-(1-hydroxy-2,6,6-trimethyl-4-oxocyclohex-2-en-1-yl)-3-methylpenta-2,4-dienoatep The title compound was prepared according to the procedure of Example 1a, substituting (±)-ABA for (S)-ABA.

Example 4b

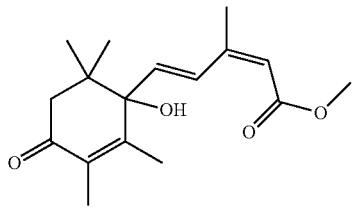 [SMILES: COC(=O)/C=C(C)\C=C\C1(O)C(C)=C(C)C(=O)CC1(C)C]

(±)-(2Z,4E)-methyl 5-(1-hydroxy-2,3,6,6-tetramethyl-4-oxocyclohex-2-en-1-yl)-3-methylpenta-2,4-dienoate The title was prepared according to the procedure of Example 1, substituting Example 4a for Example 1a.

Example 4

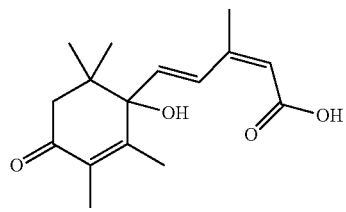 [SMILES: CC1=C(C)C(O)(/C=C/C(C)=C\C(=O)O)C(C)(C)CC1=O]

(±)-(2Z,4E)-5-(1-hydroxy-2,3,6,6-tetramethyl-4-oxocyclohex-2-en-1-yl)-3-methylpenta-2,4-dienoic acid The title compound was prepared according to the procedure of Example 2, substituting Example 4b for Example 1. $^1$HNMR (CDCl$_3$): δ7.89 (d, 1H), 6.17 (d, 1H), 5.76 (s, 1H), 2.47 (d, 1H), 2.34 (d, 1H), 2.15 (s, 1H), 2.04 (s, 3H), 1.88 (s, 3H), 1.83 (s, 3H), 1.06 (s, 3H), 1.01 (s, 3H). MS (ESI—): m/e=277. 2D-NMR experiments (COSY, NOESY, HSQC, HMBC) established that the methylation occurred at the 3'-position. Chiral HPLC analysis on a Pirkle Covalent (R,R)-Whelk-01 column with a UV detector set at 263 nm indicates that this material is composed of 49% of the (S)-isomer and 51% of the (R)-isomer.

Example 5

Seed Germination Assay

To determine the germination inhibition potency of the analogs, a germination assay was performed with the model plant *Arabidopsis thaliana*. *Arabidopsis* seed was sterilized by shaking for five minutes in 200 proof ethanol, followed by shaking for five minutes in a 10% bleach solution. The seeds were then washed five times in sterile, distilled, de-ionized water and suspended in 0.1% phytoagar. The tubes containing the seeds were wrapped in aluminum foil and stratified at 4° C. for at least two days.

The analogs were tested in four-well plates. Each plate contained one well each of a 0.5% DMSO control, (S)-ABA, (S)-3'-methyl-ABA (Example 2) and (±)-3'-methyl-ABA (Example 4), all at a desired concentration. In a typical experiment, 18 microliters of a 100 ppm stock solution of each compound in 10% DMSO was pipetted into the designated well. Additional DMSO (28.2 microliters) and water (3.8 microliters) was added to each well, followed by the addition of 5.95 mL of ½×Murashige and Skoog media containing 1.2% Bactoagar to all the wells. This gave a total volume of 6.0 mL per well, 0.3 ppm of the test compound and final DMSO concentration of 0.5%. When the media solidified, one hundred sterile stratified *Arabidopsis* seeds were distributed into each well. The plates were sealed with surgical tape and placed in a growth chamber running diurnal cycles of 12 hours of light at 24° C. and 12 hours of darkness at 19° C. The plates were scanned daily at high resolution (600 dpi) until all seeds were germinated. A seed was scored as germinated once the radicle emerged. The percentage of seeds germinated each day is reported in the graph of FIG. 1. The tests at each concentration were repeated at least twice and the results were reproducible.

As seen in FIG. 1, (S)-3'-methyl-ABA (Example 2) was more potent at inhibiting *Arabidopsis* seed germination relative to (S)-ABA or the racemic analog, (±)-3'-methyl-ABA (Example 4). The time for 100% germination was 6 days for (S)-ABA treatment, 8 days for (±)-3'-methyl-ABA treatment and 15 days for (S)-3'-methyl-ABA treatment. This biological assay is indicative of the overall agonist nature of (S)-3'-methyl-ABA compared to (S)-ABA.

Thus Applicants unexpectedly found using this assay that (S)-3'-methyl-abscisic acid was more potent than either (S)-ABA or (±)-3'-methyl-ABA. Based on the teachings of Ueno, et al, (vide supra), these results were unexpected. Additionally, based on the known functions of (S)-ABA in plant physiology, these results imply that (S)-3'-methyl-abscisic acid and the esters thereof will be more effective than (S)-ABA or (±)-3'-methyl-ABA in mediating the stomatal closure and promoting the biosynthesis of anthocyanin. Thus, this compound is expected to be more effective for fruit (e.g. grapes) coloration, thinning, protection of plants from drought stress, or other biological effects of (S)-ABA.

The invention claimed is:
1. A compound of Formula I:

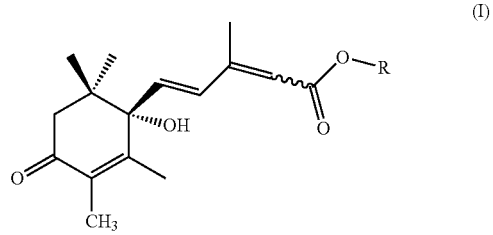

(I)

wherein R is hydrogen, substituted or unsubstituted alkyl, cycloalkyl, heterocycloalkyl, alkenylalkyl, alkynylalkyl, alkenyl, cycloalkenyl, heterocycloalkenyl, alkynyl, aryl, heteroaryl, arylalkyl, or heteroarylalkyl; and salts thereof.

2. The compound of claim 1 wherein R is hydrogen.
3. The compound of claim 1 wherein R is alkyl.
4. The compound of claim 3 wherein R is lower alkyl.
5. The compound of claim 3 wherein R is substituted with at least one of —OH, —NH$_2$, —SH, halogen, —CN, —NR$_1$R$^2$, —OR$_1$, —SR$^1$, —S(O)R$_1$, —SO$_2$R$^1$, —C(O)R$_1$, —C(O)NR$^1$R$^2$, —NHC(O)R$_1$, —NHSO$_2$R$_1$, —NHC(O)

$OR^3$, $-SO_2NR_1R^2$, or $-NHC(O)NR_1R^2$ wherein $R^1$ and $R^2$ are each independently hydrogen or lower alkyl and $R^3$ is lower alkyl.

6. The compound of claim 1 wherein the salt comprises an alkali or alkaline earth metal cation, protonated amine ($^+NHR^4R^5R^6$) wherein $R^4$, $R^5$, and $R^6$ are each independently hydrogen, lower alkyl, aralkyl or a quaternary ammonium ion ($^+NR^7R^8R^9R^{10}$) wherein $R^7$, $R^8$, $R^9$, and $R^{10}$ are each independently lower alkyl or lower aralkyl.

7. The compound of claim 1 wherein the salt comprises an inorganic anion selected from the group consisting of chloride ($Cl^-$), bromide ($Br^-$), iodide ($I^-$), sulfate ($SO_4^{2-}$), and bisulfate ($HSO_4-$), or an organic anion selected from the group consisting of formate ($HCO_2^-$), acetate ($CH_3CO_2^-$), tartrate ($^-CO_2CH(OH)CH(OH)CO_2^-$), methanesulfonate ($CH_3SO_3^-$) and tolylsulfonate ($CH_3C_6H_4SO_3^-$), and wherein R contains a basic nitrogen atom.

8. A method of regulating plant growth in *Arabidopsis* comprising applying an effective amount of the compound of claim 1 to an *Arabidopsis* plant in need of growth regulation.

9. A process of making the compound of claim 1 comprising:
   a. reacting (S)-abscisic acid with an alkylating agent to form an ester;
   b. treating the compound resulting from Step a with a base and methylating agent in a solvent;
   c. and optionally hydrolyzing the compounds resulting from Step b.

\* \* \* \* \*